United States Patent [19]
Gorog

[11] Patent Number: 5,916,813
[45] Date of Patent: Jun. 29, 1999

[54] THROMBOTIC AND/OR THROMBOLYTIC STATUS ANALYSER

[75] Inventor: Diana Adrienne Gorog, London, United Kingdom

[73] Assignee: Xylum Corporation, Scarsdale, N.Y.

[21] Appl. No.: 08/992,487

[22] Filed: Dec. 18, 1997

[30] Foreign Application Priority Data

Dec. 20, 1996 [GB] United Kingdom ................... 9626444
Jan. 15, 1997 [GB] United Kingdom ................... 9700761

[51] Int. Cl.⁶ .................................................. G01N 33/86
[52] U.S. Cl. .............................. 436/69; 436/180; 422/73; 422/100; 73/64.41
[58] Field of Search ................................ 436/63, 69, 180; 422/68.1, 73, 99, 100, 102; 435/2; 73/64.41

[56] References Cited

U.S. PATENT DOCUMENTS

| | | | |
|---|---|---|---|
| 3,748,909 | 7/1973 | Kuo | 73/864.11 |
| 3,911,728 | 10/1975 | Fixot | 73/54.04 |
| 4,780,418 | 10/1988 | Kratzer | 436/69 |
| 5,047,211 | 9/1991 | Sloane, Jr. et al. | 422/73 |
| 5,051,239 | 9/1991 | von der Goltz | 422/73 |
| 5,207,988 | 5/1993 | Lucas | 422/73 |
| 5,296,379 | 3/1994 | Gorog et al. | 436/69 |
| 5,339,830 | 8/1994 | Blake, III | 600/584 |
| 5,599,718 | 2/1997 | Gorog | 436/69 |
| 5,665,311 | 9/1997 | Gorog et al. | 422/73 |

OTHER PUBLICATIONS

Gorog et al. *Thrombosis and Haemostasis*, vol. 73, No. 3, pp. 514–520, 1995.

*Primary Examiner*—Maureen M. Wallenhorst
*Attorney, Agent, or Firm*—Pillsbury Madison & Sutro LLP

[57] ABSTRACT

A method of analyzing thrombotic activity of blood samples that includes providing a capillary tube between a vessel containing a sample of blood and a collection reservoir, applying pressure to the blood to draw it from the vessel through the capillary tube and into the reservoir for a predetermined period of time, and measuring the blood collected in the reservoir within the predetermined time period as an indication of the platelet activity of the blood sample. By following these simple steps it is possible to produce measurements which are meaningful and physiologically relevant.

14 Claims, 2 Drawing Sheets

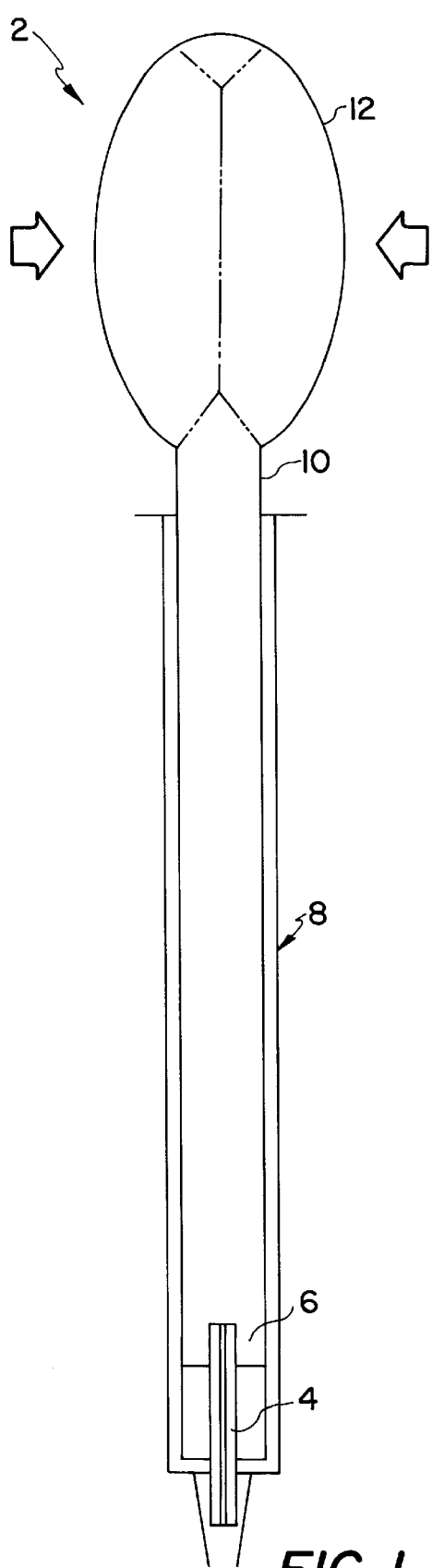
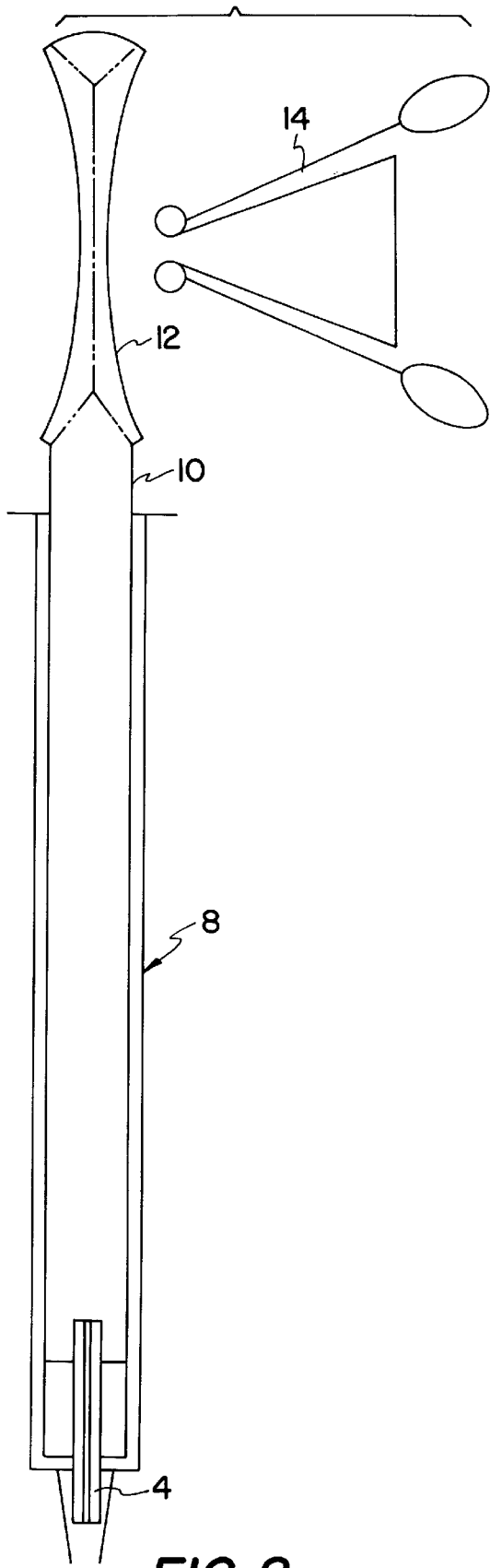
FIG. 1    FIG. 2

THROMBOTIC AND/OR THROMBOLYTIC STATUS ANALYSER

RELATED APPLICATIONS

This application claims priority from UK application Nos. 9626444.5, filed Dec. 20, 1996, and 9700761.1, filed Jan. 15, 1997, the disclosures of which are incorporated herein by this reference.

BACKGROUND OF THE INVENTION

1. Field of the Invention

This invention relates to an in vitro method of analysing the thrombotic and thrombolytic activity of blood. In particular it relates to a method and apparatus for rapidly and simply assessing the capacity for shear-induced platelet aggregation in native blood.

2. Description of the Related Art

The degree to which platelet aggregation occurs in a sample of blood taken from a patient is an indicator of the likelihood of the risk to the patient of, at one extreme, haemorrhage and the other, thrombosis. An example of the former would be the bleeding disorder of Willebrand disease and. haemophilia which results from a low level of Factor VIII, a blood clotting protein, An example of the latter., would be advanced artherosclerosis where hyper-reactivity of platelets has been documented. Patients with increased fibrinolytic potential, such as after coronary artery bypass surgery are at risk of excessive bleeding, while decreased fibrinolytic potential i.e. reduced ability to spontaneously dissolve a thrombus may lead to lasting occlusion and myocardial infarction.

There are many known techniques for measuring fibrinolysis. Generally however fibrinolysis assays such as the lysis time of plasma proteins,clot made from whole plasma or whole blood are laborious and time-consuming and therefore rarely used in clinical practice. Fibrinolytic status is normally assessed by the factorial approach wherein at least half a dozen plasma variables are measured. The list of necessary variables is constantly increasing and the assessment of the overall status from the individual variables is extremely difficult.

There are also known techniques for measuring haemostasis i.e. the process of blood protein interaction and cellular activation which leads to the formation of a platelet plug and subsequently to the production of a fibrin-platelet clot at the sight of a tissue injury whereby bleeding is halted and vascular integrity restored. For example European Patent Application No. 0129425 describes a laboratory technique for measuring haemostasis. A polyethylene tube connected to a syringe of fresh blood is punctured with a small hole to simulate bleeding. The bleeding through the hole and clotting time in the tube are monitored. With this arrangement human blood samples can be monitored and evaluated with and without the presence of various agents which promote haemostasis or thrombolytic activity. In a development of this technique as described in PCT/GB87/00633, multiple channels of tubing are connected to individual syringes of freshly drawn blood, which channels are simultaneously punctured by a common punching needle. This permits the concurrent measurement of haemostasis and the expulsion of the haemostatic plug i.e. thrombolysis provided that coagulation of the blood is prevented by an anticoagulant.

In another method described in U.S. Pat. No. 4,780,418, blood to be tested is drawn into a capillary tube under a given reference pressure which is produced with a sophisticated control feedback whereby the amount of blood flowing in the capillary is measured as an indication of the aggregation of the blood platelets. Later workers have sought to ensure that thrombus formation takes place at a precisely defined location in the measuring apparatus by providing an aperture through which blood is passed from a capillary tube, the aperture being formed in a porous member which is generally soaked in a solution which activates the platelets.

In the Applicant's own European Patent Application No. 9390027.6, there is described a method for measuring thrombotic and thrombolytic activity of whole blood in which again blood is drawn under pressure through a capillary tube. However, conditions are arranged such that thrombus formation occurs in the capillary tube solely by shear stress. Once the tube has been occluded by the formed thrombus, the pressure is reduced and the thrombus allowed to stabilise for a period of time. The pressure is then reversed and lysis i.e. dislodgement of the thrombus is monitored by detecting restoration of flow through the tube.

The method disclosed in European Patent Application No. 93900279.6 has been found to provide accurate results relevant to the in vivo situation. However the method like all other physiologically relevant techniques known to the Applicant suffers from the disadvantage that it is time consuming. In particular, the thrombolysis measurement takes a considerable time, up to 90 min, and, until it occurs, the instrument cannot be used for testing another blood sample. Known techniques do not allow for rapid and ready analysis and so are not suitable for use in clinics and the like where many patients are to be tested in a day.

There therefore exists a need for a simple device which allows the evaluation of the test result immediately and is suitable for testing the population at large.

SUMMARY OF THE INVENTION

It is an object of the present invention to provide a method which allows analysis to be made quickly and easily by a single person and which produces uniform repeatable results. It is a further object to provide such a method which involves the use of apparatus which is completely disposable to prevent the spread of disease carried by infected blood which is being tested. The apparatus should also preferably be inexpensive, versatile and small scale.

In accordance with one aspect of the invention a method of analysing thrombotic activity of blood samples comprises providing a capillary tube between a vessel containing a sample of blood and a collection reservoir, applying pressure to the blood to draw it from the vessel through the capillary tube and into the reservoir for a predetermined period of time and measuring the blood collected in the reservoir within the predetermined time period as an indication of the platelet activity of the blood sample.

It has surprisingly been found that with a method simply involving these steps it is possible to produce measurements which are meaningful and physiologically relevant. The method can be carried out relatively quickly, the preferred time period being five minutes and can be conducted by a single person, in particular a nurse or other technician who has taken a blood sample from a patient.

The method does not involve the use of complicated apparatus and so there is no requirement for a sophisticated pressure-control mechanism nor for providing a thrombus formation site. In particular the blood preferably flows directly from the outlet of the capillary tube into the reservoir and does not pass through any aperture or the like provided adjacent the outlet of the tube. Thrombus formation occurs in the lumen of the capillary tube solely by the flow-generated shear-forces.

The method is carried out on non anti-coagulated (native) blood.

It has been found that there is no need to maintain the applied pressure accurately since it is the initial pressure which is the main determinant of the rate of thrombus formation. The optimal initial pressure is 50–90 mmHg.

In accordance with another aspect of the invention a method of analysing thrombolytic activity of blood samples comprises forming a thrombus from a blood sample within a capillary tube by flowing blood through the tube from an inlet thereof to an outlet thereof by applying negative pressure to the outlet, inserting the inlet in a reservoir of saline solution, applying negative pressure to the inlet across the saline solution, detecting blood flow from the inlet as an indication of lysis of the thrombus and measuring the time between application of the negative pressure and lysis.

With this second aspect of the invention it has again been found possible to produce meaningful and physiologically relevant measurements without the use of complicated apparatus in particular without any requirement for accurate pressure control.

The two aspects are preferably combined to provide a method for analysing both the thrombotic and thrombolytic activity of blood samples.

Apparatus suitable for carrying out a method in accordance with the first aspect of the invention comprises a vessel for containing a blood sample, a capillary tube with an inlet communicating with the vessel and a outlet communicating directly with a collection reservoir, means for applying pressure across the capillary tube such that blood from a sample in the vessel is drawn through the capillary tube and into the reservoir, and means for measuring the amount of blood collected in the reservoir following application of pressure across the capillary tube.

Apparatus suitable for carrying out a method in accordance with the second aspect of the invention or the combined first and second aspects comprises a capillary tube with an inlet and an outlet, a first vessel for containing a blood sample, a second vessel for containing saline solution, the capillary inlet being alternatively communicable with the first and second vessels to connect it to the blood sample and saline solution respectively, means for applying a negative pressure to the outlet, means for measuring blood flow through the capillary with the inlet connected to the blood sample in the first vessel, means for applying a negative pressure to the capillary inlet when connected to the saline solution across the saline solution, and means for detecting blood flow from the capillary inlet with the inlet connected to the saline solution.

The means for applying a negative pressure to the outlet is very preferably separate and distinct from the means for applying a negative pressure to the inlet of the capillary. In either case the pressure applying means is also preferably directly connected without any valves or other pressure control devices. As noted above it has been found that valves or other pressure control devices are not necessary and this greatly increases the simplicity of the system. In a particularly preferred embodiment the pressure applying means is a compressed bulb activated by release of the bulb such as for example a compressed Pasteur pipette.

BRIEF DESCRIPTION OF THE DRAWINGS

The invention will now be further described by way of example with reference to the accompanying drawings in which:

FIGS. 1 and 2 are respectively front and side views of an apparatus for analysing thrombotic activity.

DETAILED DESCRIPTION OF THE PRESENTLY PREFERRED EXEMPLARY EMBODIMENTS

Figure 3:
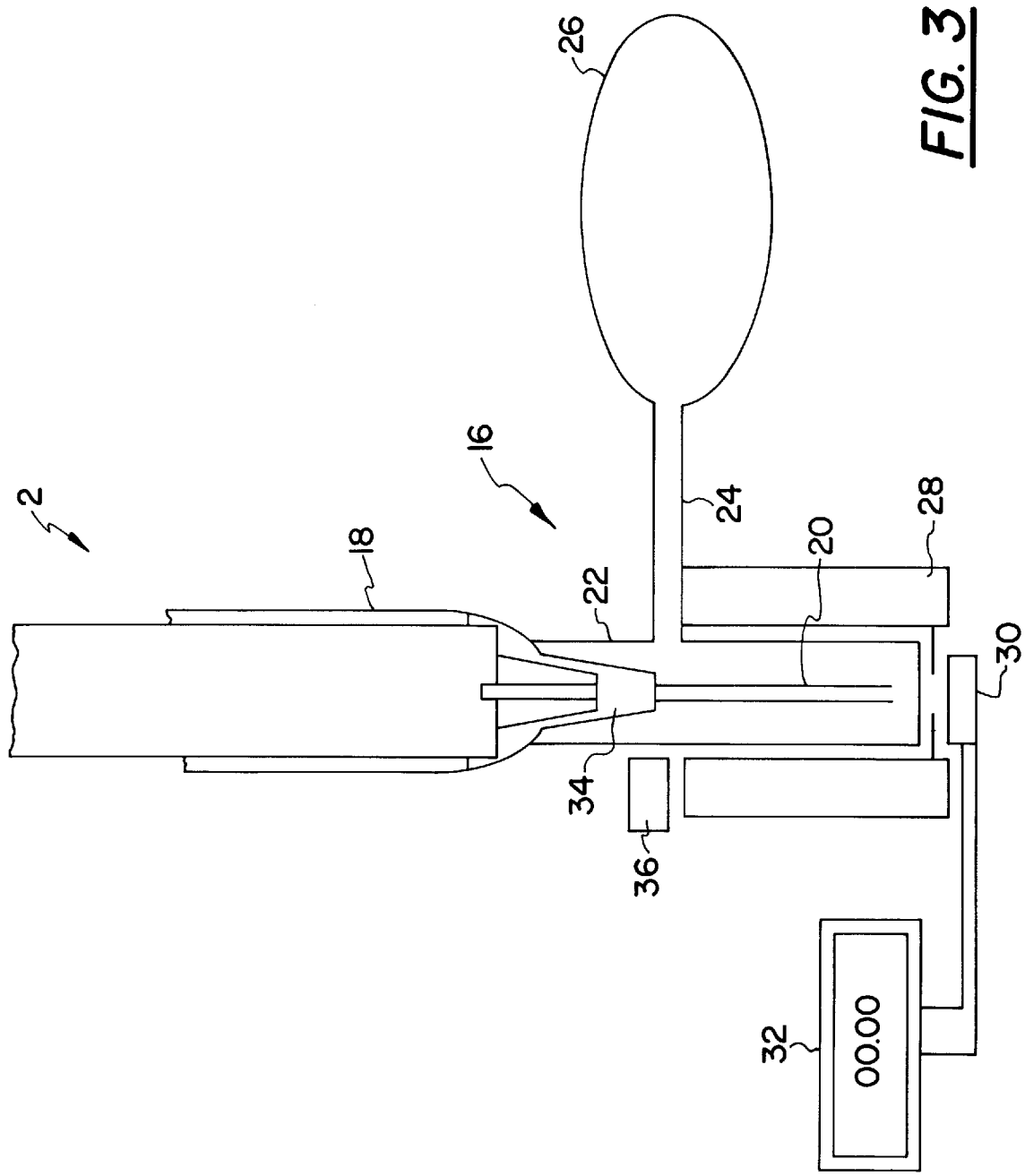
FIG. 3 is a front view of an apparatus for analysing thrombolytic activity.

The thrombotic activity analysing apparatus 2 comprises a capillary tube 4 which is preferably formed from the plastic PEEK and may have for example a 0.005 inch inner diameter and a 0.062 inch outer diameter. A suitable length for the capillary tube 4 is 5–20 mm, preferably 15 mm.

In use blood flows from the lower, and therefore inlet, end of the capillary tube 4 to the upper outlet end and thence to a collection reservoir 6. As illustrated in FIGS. 1 and 2 the collection reservoir 6 may conveniently be provided by inserting the capillary tube 4 into the barrel of a syringe 8 in which it is held by a silicon tubing collar 10.

Blood flow through the capillary tube 4 is caused by application of a negative pressure thereto. As illustrated the pressure may be conveniently provided by use of a Pasteur pipette 10 cut below the bulb and pushed into the upper end of the barrel of the syringe 8. The pipette 10 can be sealed to the barrel of the syringe 8 using UV curing glue. Prior to use the bulb 12 of the pipette 10 is compressed using a clip 14.

The blood to be tested can be in a test tube or the syringe can be inserted into the luer-fitting of a catheter cited in a patient's vein.

A method of operation of the apparatus 2 will now be described. The apparatus is prepared prior to blood-taking by compressing the bulb 12 of the pipette 10 with the foldback clip 14. Blood is taken by the standard technique and the first 2 ml or so of blood is discarded or used for full blood count measurement. The luer of the apparatus 2 is then inserted into the fitting of the catheter, the clip 14 removed and a stop clock started.

Alternatively, 1 ml blood is taken and transferred from the syringe into a PTFE or Teflon test tube preheated to 37° C. in a dry block heater. The inlet of apparatus 2 is then immersed int the test tube containing the blood sample before the clip 14 is removed and the timing started.

Removal of the clip 14 causes application of a vacuum in the syringe 10 which forces the blood to flow from the catheter through the capillary tube 4 into the syringe 10. In the capillary lumen, shear stress and platelet aggregation result in an occlusive thrombus formation which would eventually arrest blood flow.

The test is continued for a predetermined period of time, for example five minutes, after removal of the clip 14 and the syringe 10 (together as appropriate with the catheter) is then removed from the patient. The volume of blood in the reservoir 6 constituted by the syringe 10 is determined, preferably by means of a visual scale provided on the syringe 10. By comparison with a known range of blood volume for normal thrombotic reaction, an assessment can be made of the risk of bleeding or thrombosis which would be indicated respectively by larger or smaller volumes collected within the given time period.

The apparatus 2 is extremely simple, small scale and fully disposable. It can readily and quickly be operated and enables a rapid but meaningful assessment of platelet aggregation activity of blood.

FIG. 3 shows an apparatus 16 for analysing thrombolytic activity i.e. dislodgement of a thrombus. The thrombolytic analysing apparatus. 16 comprises a funnel-shaped vessel 20 which has an outlet in the form of a luer fitting continuing into a narrow tube 22. The lower part of the vessel 18 sits in and is connected to the mouth of a tubular container 22 which has a side arm 24 connected to a pipette bulb 26. The vessel 18 and container 22 are both preferably made of plastic and disposable.

The container 22 is surrounded by a metal block heater 28 which is held at 37° C. A photosensor 30 is positioned in an aperture at the bottom of the heater 28 and is connected to a digital timer 32 via an amplifying circuit (not shown).

A method of operating the apparatus 16 for thrombolytic activity measurement will now be described. The apparatus 16 is prepared by compressing the bulb 26 with a fold-back clip and placing saline 34 in the vessel 18.

The capillary tube 4 and syringe 8 of an apparatus 2 which has already been used to form an occlusive thrombus in the capillary tube 4 is then inserted in the vessel 18. The bulb 12 of the thrombotic analysing apparatus 2 is pierced to release the remaining vacuum and to ensure atmospheric pressure in the system. The clip is removed from the bulb 26 and the timer 32 started. At this stage a light source 36 illuminates the photosensor 30 and this current is supplied to the timer 32. The thrombus within the capillary 4 will however gradually lyse and will then no longer resist the negative pressure applied by the bulb 26. Blood will therefore flow from the syringe 8 into the tube 20. Once the tube 20 has filled with blood, it will drip into the bottom of the container 22 covering the aperture in the heater 28 and causing a drastic reduction in the light signal to the photosensor 30. The current to the timer 32 will cease, stopping the timing and finishing the measurement.

The apparatus 16 provides for a standard analysis of thrombolytic activity. As with the apparatus 2 it is simple, small scale and the blood contacting parts thereof, vessel 18, tube 20 and container 22, are fully disposable. It is simple to operate.

Both thrombotic analysing apparatus 2 and thrombolytic analysing apparatus 16 have in common the feature that the pressure is applied through use of a compressible bulb. There is no complicated valving or pressure control devices nor is there any need to provide a system which can reverse the direction of the applied pressure. This makes both thrombotic and thrombolytic testing simpler, cheaper and easier. The thrombotic analysing apparatus requires no electric current whilst the thrombolytic analysing apparatus can be operated by battery, so the whole system is versatile and suitable for field studies.

We claim:

1. A method of analysing platelet aggregation activity of blood samples comprising:
   providing a capillary tube between a vessel containing a sample of blood and a collection reservoir;
   applying pressure to the blood to draw the blood from the vessel, through the capillary tube, and into the reservoir for a predetermined period of time; and
   measuring the blood collected in the reservoir within the predetermined time period as an indication of the platelet aggregation activity of the blood sample;
   wherein the pressure is applied to the blood at a capillary tube outlet, without any valves or pressure control devices.

2. A method as claimed in claim 1 wherein the blood flows directly from an outlet of the capillary tube into the reservoir.

3. A method as claimed in either claim 1 or claim 2 wherein the blood of the sample is non anti-coagulated.

4. A method as claimed in claim 3 wherein the pressure applied is 50–90 mmHg.

5. A method as claimed in claim 3 wherein the predetermined time period is 5 minutes.

6. A method of analysing the thrombolytic activity of blood samples comprising:
   forming a thrombus from a blood sample within a capillary tube by flowing blood through the tube from an inlet thereof to an outlet thereof by applying a first negative pressure to the outlet;
   inserting the inlet in a reservoir of saline solution;
   applying a second negative pressure to the inlet across the saline solution;
   detecting blood flow from the inlet as an indication of lysis of the thrombus; and
   measuring the time between application of the second, negative pressure and lysis.

7. A method as claimed in claim 6 wherein the second negative pressure applied to the inlet of the capillary tube is greater than the first negative pressure.

8. Apparatus for analysing the platelet aggregation of blood samples comprising:
   a vessel for containing a blood sample;
   a capillary tube with an inlet communicating with the vessel and an outlet communicating directly with a collection reservoir;
   means for applying a first pressure across the capillary tube such that blood from a sample in the vessel is drawn through the capillary tube and into the reservoir; and
   means for measuring the amount of blood collected in the reservoir following application of the first pressure across the capillary tube;
   wherein the first pressure applying means is directly connected to an outlet of the capillary tube, without any valves or pressure control devices.

9. Apparatus as claimed in claim 8 wherein the vessel comprises a catheter connected to a patient's vein for drawing the blood sample to be tested.

10. Apparatus for analysing the thrombolytic activity of blood samples comprising:
    a capillary tube with an inlet and an outlet;
    a first vessel for containing a blood sample;
    a second vessel for containing saline solution;
    the capillary inlet being alternatively communicable with the first and second vessels to connect the capillary tube to the blood sample and saline solution, respectively;
    means for applying a first negative pressure to the outlet of the capillary tube, means for measuring blood flow through the capillary tube with the inlet connected to the blood sample in the first vessel;
    means for applying a second negative pressure to the capillary inlet when connected to the saline solution in the second vessel across the saline solution; and
    means for detecting blood flow out of the capillary inlet when the capillary inlet is connected to the saline solution in the second vessel.

11. Apparatus as claimed in claim 10 wherein the means for applying a first negative pressure to the outlet of the capillary tube is separate and distinct from the means for applying a second negative pressure to the inlet of the capillary tube.

12. Apparatus as claimed in any one of claims 10 to 11 wherein the first pressure applying means is directly connected to the capillary tube outlet, without any valves or pressure control devices.

13. Apparatus as claimed in claim 12 wherein the first pressure applying means is a compressed bulb activated by release of the bulb.

14. Apparatus as claimed in claim 8 or claim 10 wherein the first pressure applying means is a compressed bulb activated by release of the bulb.

* * * * *